US00PP11080P

United States Patent [19]

van Dongen

[11] Patent Number: Plant 11,080

[45] Date of Patent: Oct. 5, 1999

[54] DAHLIA PLANT NAMED 'FLEUREL'

[75] Inventor: Esther van Dongen, Zwaanshoek, Netherlands

[73] Assignee: P.J.M. van Schie V.O.F., Voorhout, Netherlands

[21] Appl. No.: 09/044,758

[22] Filed: Mar. 20, 1998

[51] Int. Cl.[6] ..... A01H 5/00

[52] U.S. Cl. ..... Plt./321

[58] Field of Search ..... Plt./321

[56] References Cited

U.S. PATENT DOCUMENTS

P.P. 1,386 4/1955 Curtis et al. ..... Plt./321

OTHER PUBLICATIONS

GTITM UPOVROM Citation for 'Fleur' as per GB BIL 09900102; 1997.

GTITM UPOVROM Citation for 'Fleurel' as per QZ PBR 970506; Apr. 15, 1997.

*Primary Examiner*—Howard J. Locker
*Assistant Examiner*—Kent L. Bell
*Attorney, Agent, or Firm*—C. A. Whealy

[57] ABSTRACT

A distinct cultivar of Dahlia plant named 'Fleurel', characterized by its large fully double pure white inflorescences and relatively compact growth habit.

2 Drawing Sheets

BACKGROUND OF THE INVENTION

The present invention relates to a new and distinct variety of Dahlia plant, botanically known as *Dahlia hybrida,* and hereinafter referred to by the name 'Fleurel'.

The new Dahlia is a naturally-occurring mutation of the yellow-flowered *Dahlia hybrida* 'Kelvin Floodlight' (not patented). In August, 1994, the new Dahlia was discovered by the inventor in a controlled environment in Zwaanshoek, The Netherlands, within a population of plants of 'Kelvin Floodlight'. The selection of this plant was based on its large white double flowers and compact plant habit.

Asexual reproduction of the new Dahlia by tubers or cuttings harvested at a controlled environment in Zwaanshoek, The Netherlands, has shown that the unique features of this new Dahlia are stable and reproduced true to type in successive generations.

BRIEF SUMMARY OF THE INVENTION

The new Dahlia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Fleurel'. These characteristics in combination distinguish 'Fleurel' as a new and distinct cultivar:

1. Large fully double pure white inflorescences.
2. Relatively compact growth habit.

The new Dahlia has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a close-up view of a typical inflorescence of the new Dahlia.

The top photograph on the second sheet comprises a close-up view of typical ray florets of 'Fleurel'.

The lower photograph on the second sheet comprises a close-up view of compound leaves (left) and single leaves (right). Floret and foliage colors may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown outdoors in Zwaanshoek, The Netherlands, during the summer under commercial practice after storing tubers at 5 to 9° C. from the end of October to January.

Botanical classification: *Dahlia hybrida* 'Fleurel'.

Parentage: Naturally-occurring mutation of *Dahlia hybrida* 'Kelvin Floodlight'.

Propagation:

*Type.*—By tubers or by cuttings.

*Time to rooting, tubers, summer.*—About 14 to 21 days with soil temperatures of 10 to 15° C.

*Rooting habit.*—Propagates easily, roots fibrous and well-branched.

Plant description:

*Appearance.*—Perennial garden plant. Bushy with stems upright. Upright and relatively compact growth habit. Moderate growth rate and moderately vigorous. Few branches, pinching will increase branching. From planting outdoors at the end of May, plants will usually flower about 10 to 12 weeks later.

*Plant height.*—About 80 cm.

*Plant spread.*—About 60 cm.

*Stem description.*—Internode length: About 7 cm. Diameter: 2.5 cm. Texture: Very smooth. Color: 144A/144B.

*Foliage description.*—Arrangement: Young foliage, leaves single; fully expanded foliage, leaves compound, trifoliate. Leaf length: About 22.5 cm. Leaf width: About 20 cm. Leaflet length: About 11 cm. Leaflet width: About 10 cm. Leaf/leaflet shape: Ovate. Leaf/leaflet apex: Cuspidate. Leaf/leaflet base: Truncate. Leaf/leaflet margin: Serrate or doubly serrate. Primary petiole length: About 4.5 cm. Color: Young foliage, upper surface: 146A/146B. Young foliage, lower surface: 138B. Fully expanded foliage, upper surface: 146A/146B. Fully expanded foliage, lower surface: 138B. Petiole: 143A.

Flowering description:

*Appearance.*—Fully double inflorescence form. Inflorescences hemispherical and borne on terminals above foliage, arising from leaf axils. Disc and ray florets arranged acropetally on a capitulum.

*Flowering response.*—Under natural conditions, plants flower intermittently during August/September in the Northern Hemisphere.

*Flower longevity.*—From opening, about three weeks.

*Quantity of inflorescences per plant.*—Typically three to four or if plants are pinched eight to ten.

*Fragrance.*—None.

*Flower bud* (*just before opening*).—Shape: Globular. Length: About 15 cm. Diameter: About 2.25 cm. Color: Close to 144C.

*Inflorescence size.*—Diameter: About 22.5cm. Depth (height): About 15 cm.

*Ray florets.*—Shape: Oblanceolate. Length: About 10 cm. Width: About 5 cm. Apex: Mucronate. Margin: Entire. Texture: Satiny, glabrous. Number of ray florets per inflorescence: About 150 arranged in about 15 to 20 rows. Color: Upper surface: 155A; base (1 cm), 2A. Under surface: 155A; base (1 cm), 2A.

*Disc florets.*—Shape: Elongated, cylindrical. Length: about 1.5 cm. Width: About 2.5 mm. Number of disc florets per inflorescence: About 30 arranged in about four rows. Color: Apex: 23A. Base: 145D.

*Peduncle.*—Aspect: Erect and strong. Length: About 24.5 cm. Diameter: About 6 mm. Color: 143A.

*Sepals.*—Shape: Oblong. Tip: Acute to obtuse. Margin: Entire. Color: 137B/137C to 144C/144D.

*Reproductive organs.*—Androecium: Anther length: About 5 mm. Anther width: About 1 mm. Anther color: 23A. Pollen color: 23A. Gynoecium: Style length: About 5 mm. Style color: 144C. Stigma color: 23B.

Disease resistance: No known Dahlia diseases observed to date on plants grown under commercial greenhouse conditions.

Seed production: Seed production has not been observed.

It is claimed:

1. A new and distinct cultivar of Dahlia plant named 'Fleurel', as illustrated and described.

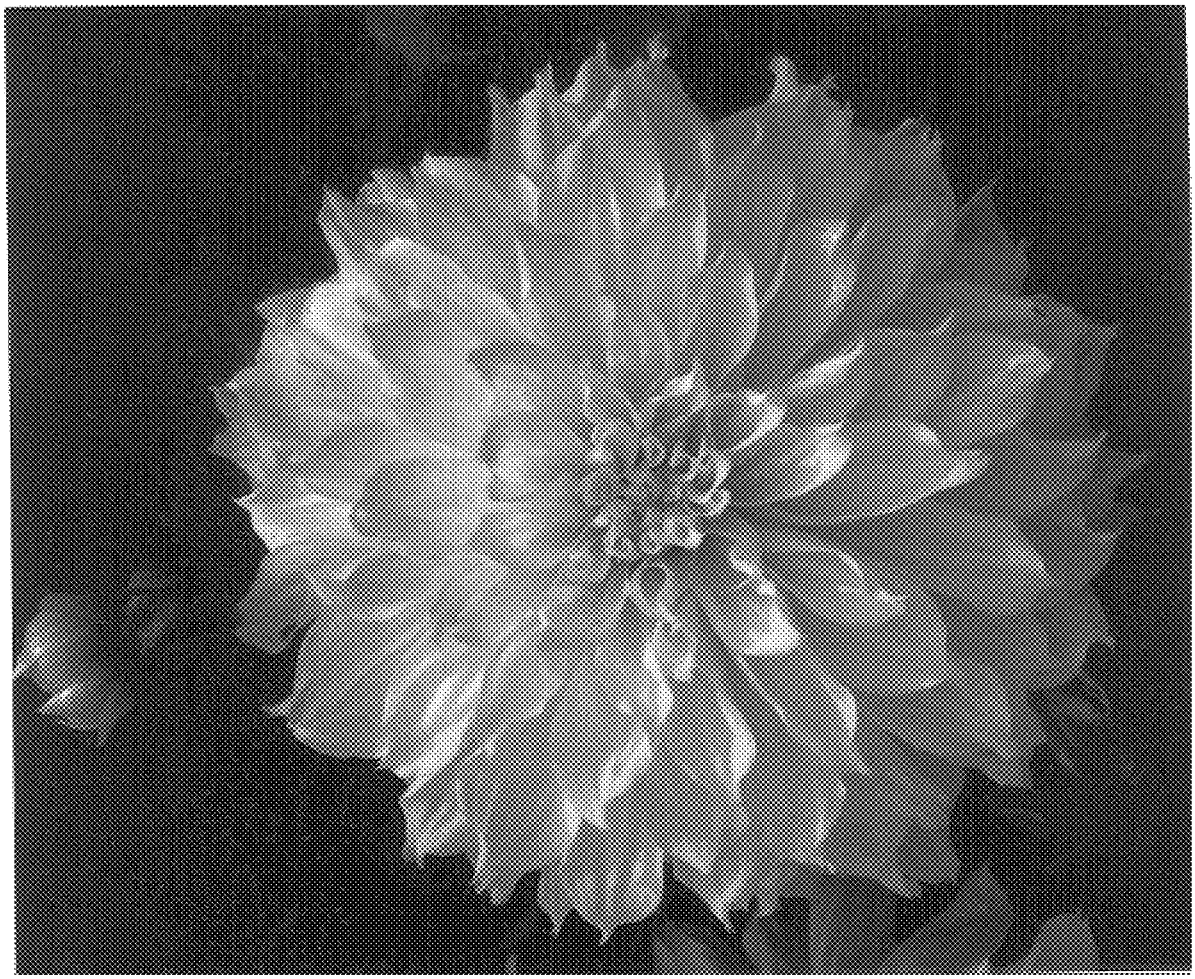

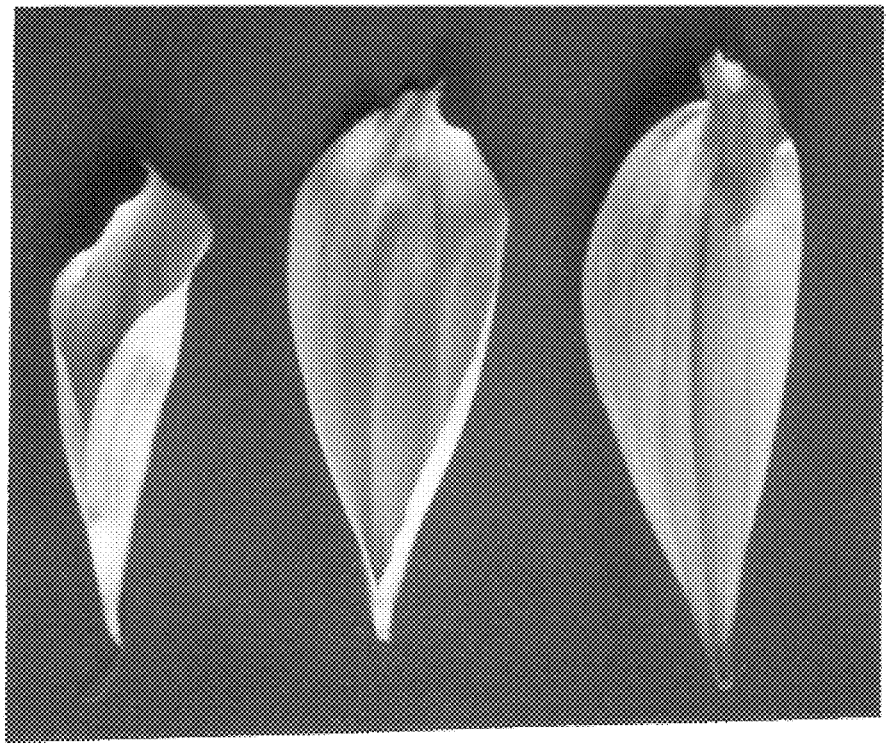
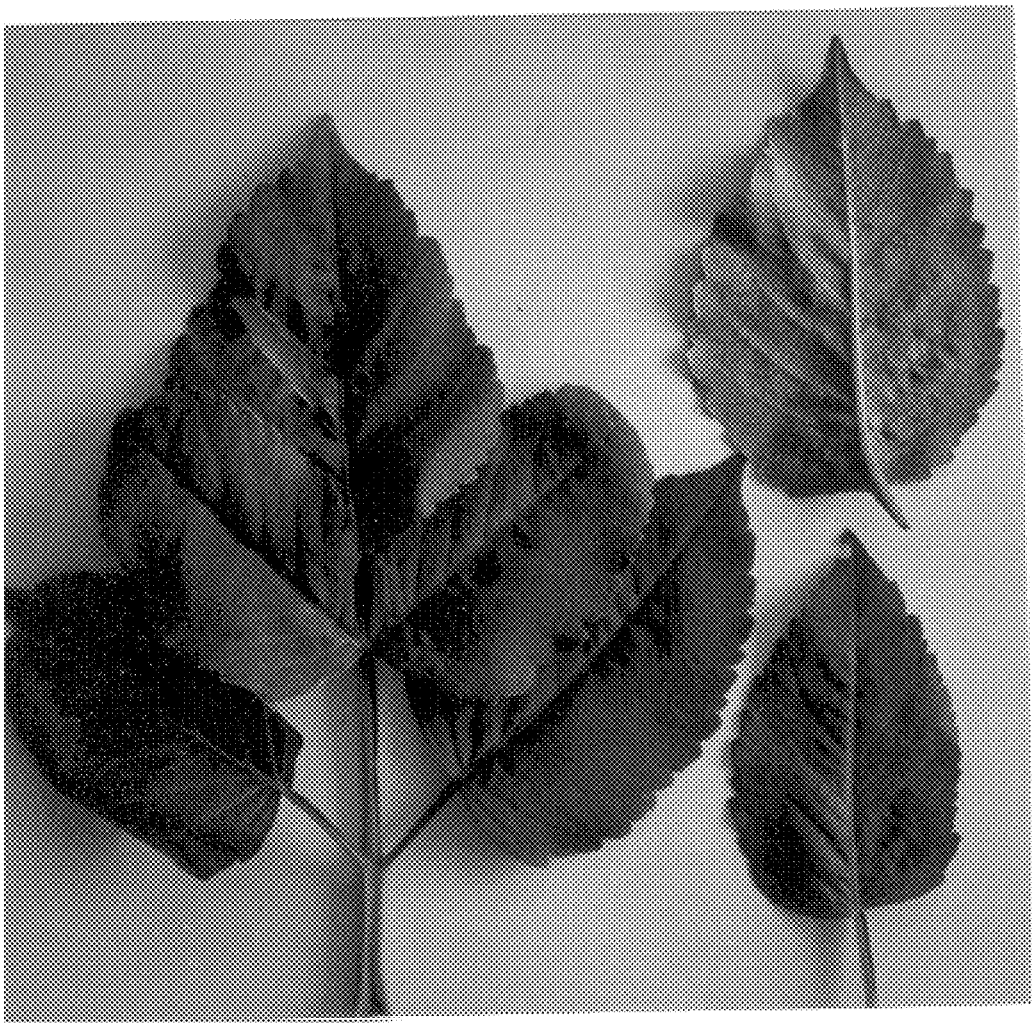

* * * * *